United States Patent
Ludewig et al.

(10) Patent No.: US 9,255,067 B2
(45) Date of Patent: Feb. 9, 2016

(54) PROCESS FOR PREPARING LOW-VISCOSITY ALLOPHANATES CONTAINING ACTINICALLY CURABLE GROUPS

(75) Inventors: Michael Ludewig, Köln (DE); Jan Weikard, Odenthal (DE)

(73) Assignee: Allnex IP S.ar.L., Luxembourg (LU)

( * ) Notice: Subject to any disclaimer, the term of this patent is extended or adjusted under 35 U.S.C. 154(b) by 872 days.

(21) Appl. No.: 11/243,126

(22) Filed: Oct. 4, 2005

(65) Prior Publication Data

US 2006/0079660 A1  Apr. 13, 2006

(30) Foreign Application Priority Data

Oct. 7, 2004  (DE) .......................... 10 2004 048 873

(51) Int. Cl.
| | |
|---|---|
| C07C 269/02 | (2006.01) |
| C07C 269/06 | (2006.01) |
| C07C 273/18 | (2006.01) |
| C08G 18/67 | (2006.01) |
| C08G 18/73 | (2006.01) |
| C08G 18/75 | (2006.01) |
| C08G 18/78 | (2006.01) |
| C08G 18/28 | (2006.01) |
| C09D 175/16 | (2006.01) |

(52) U.S. Cl.
CPC ......... *C07C 273/1836* (2013.01); *C07C 269/02* (2013.01); *C07C 269/06* (2013.01); *C08G 18/284* (2013.01); *C08G 18/2835* (2013.01); *C08G 18/672* (2013.01); *C08G 18/6715* (2013.01); *C08G 18/73* (2013.01); *C08G 18/755* (2013.01); *C08G 18/758* (2013.01); *C08G 18/7837* (2013.01); *C09D 175/16* (2013.01)

(58) Field of Classification Search
USPC ........ 522/90, 96, 97, 174; 525/123, 124, 125, 525/126, 127, 130, 453, 455, 457, 458, 525/460; 526/301, 302; 528/44, 45, 49, 59, 528/75; 564/44, 45, 46; 560/330, 336, 355; 523/115, 116; 252/182.18, 182.2
IPC ............ C07C 269/02,269/06, 273/1836; C08G 18/2835, 18/284, 18/6715, 18/672, 18/73, C08G 18/755, 18/758, 18/7837; C09D 175/16
See application file for complete search history.

(56) References Cited

U.S. PATENT DOCUMENTS

| | | | |
|---|---|---|---|
| 4,160,080 | A | 7/1979 | Köenig et al. ................. 528/59 |
| 5,596,065 | A | 1/1997 | Gerlitz et al. .................. 528/71 |
| 5,672,736 | A | 9/1997 | Brahm et al. ................ 560/345 |
| 5,739,251 | A | 4/1998 | Venham et al. ................ 528/49 |
| 5,777,024 | A | 7/1998 | Killilea et al. .............. 524/590 |
| 5,917,083 | A | 6/1999 | König et al. ................. 560/157 |
| 5,951,911 | A | 9/1999 | Venham et al. ........... 252/182.2 |
| 6,392,001 | B1 | 5/2002 | Mertes et al. .................. 528/59 |
| 6,617,413 | B1 | 9/2003 | Bruchmann et al. ........... 528/75 |
| 7,037,972 | B2 * | 5/2006 | Nienhaus et al. ............ 524/507 |
| 7,361,723 | B2 * | 4/2008 | Detrembleur et al. ......... 528/48 |
| 7,666,970 | B2 * | 2/2010 | Weikard et al. ................ 528/48 |
| 8,853,295 | B2 * | 10/2014 | Ludewig et al. ............. 522/174 |
| 2003/0153713 | A1 | 8/2003 | Spyrou et al. .................. 528/48 |
| 2004/0068081 | A1 | 4/2004 | Facke et al. .................... 528/73 |
| 2005/0209427 | A1 * | 9/2005 | Detrembleur et al. ......... 528/44 |

FOREIGN PATENT DOCUMENTS

| | | |
|---|---|---|
| DE | 10 2004 012 903 | 3/2004 |
| EP | 0 899 283 A2 | 3/1999 |
| GB | 994890 | 6/1965 |
| WO | WO 02/26853  * | 4/2002 |

OTHER PUBLICATIONS

B. Vollmert, "Synthesis of Polymers with C—C Chains by the Polymerization of Olefinically Unsaturated Compounds," *Grundriss der makromolekularen Chemie*, (1979), vol. 1, Section 2.1 and Table 55, pp. 52-55.

* cited by examiner

*Primary Examiner* — Rabon Sergent
(74) *Attorney, Agent, or Firm* — Drinker Biddle & Reath LLP

(57) ABSTRACT

The present invention provides a process for preparing radiation-curing allophanates having residual monomer contents of less than 0.5% by weight and an NCO content of less than 1% by weight, wherein (A) compounds containing isocyanate groups, (B) hydroxy-functional compounds which contain groups which react, with polymerization, with ethylenically unsaturated compounds on exposure to actinic radiation (radiation-curing groups) and (C) optionally further compounds containing NCO-reactive groups, also optionally in the presence of a catalyst, are used to form NCO-group-containing urethanes having radiation-curing groups, which are subsequently reacted, without further addition of compounds containing isocyanate groups, in the presence of an allophanatization catalyst, the ratio of NCO groups of the compounds from A) to the OH groups of the compounds from B) and, where used, C) being 1.45:1.0 to 1.1:1.0.

12 Claims, No Drawings

PROCESS FOR PREPARING LOW-VISCOSITY ALLOPHANATES CONTAINING ACTINICALLY CURABLE GROUPS

CROSS-REFERENCE TO RELATED APPLICATION

This application claims priority to Germany Application DE 10 2004 048 873.8, filed Oct. 7, 2004.

FIELD OF THE INVENTION

The present invention relates to a simplified process for preparing low-viscosity reaction products of polyisocyanates containing activated groups which react, with polymerization, with ethylenically unsaturated compounds on exposure to actinic radiation.

BACKGROUND OF THE INVENTION

The curing of coating systems which carry activated double bonds by actinic radiation, such as UV light, IR radiation or else electron beams, is known and is established in industry. It is one of the most rapid curing methods in coating technology. Coating compositions based on this principle are thus referred to as radiation- or actinically curing or curable systems.

Because of the environmental and economic requirements imposed on modern coating systems, that they should use as little organic solvents as possible, or none at all, for adjusting the viscosity, there is a desire to use coatings raw materials which are already of low viscosity. Known for this purpose for a long time have been polyisocyanates with an allophanate structure as are described, inter alia, in EP-A 0 682 012.

In industry these substances are prepared by reacting a monohydric or polyhydric alcohol with large amounts of excess aliphatic and/or cycloaliphatic diisocyanate (cf. GB-A 994 890, EP-A 0 000 194 or EP-A 0 712 840). This is followed by removal of unreacted diisocyanate by means of distillation under reduced pressure. According to DE-A 198 60 041 this procedure can also be carried out with OH-functional compounds having activated double bonds, such as hydroxyalkyl acrylates, although difficulties occur in relation to the preparation of particularly low-monomer-content products. Since the distillation step has to take place at temperatures up to 135° C., in order to be able to lower the residual isocyanate content sufficiently (<0.5% by weight of residual monomer), it is possible for double bonds to react, with polymerization, under thermal initiation, even during the purification process, meaning that ideal products are no longer obtained.

The preparation of low-monomer-content, allophanate-containing, polyurethane-based, radiation-curing binders is described in EP-A 0 867 457 and U.S. Pat. No. 5,739,251. These binders, however, do not carry activated double bonds but instead carry unreactive allyl ether groups (structure R—O—CH$_2$—CH=CH$_2$). It is therefore necessary to add reactive diluents (low molecular weight esters of acrylic acid), which introduce the required UV reactivity.

There has also been no paucity of attempts to prepare allophanates indirectly, from other isocyanate derivatives, urethanes and isocyanates. For instance, EP-A 0 825 211 describes a process for synthesizing allophanate structures from oxadiazinetriones, although no mention is made there of radiation-curing derivatives containing activated double bonds. Transposition to the particular circumstances of radiation-curing systems is described in German application No.: 10246512.6, unpublished at the priority date of the present specification.

Another route is the opening of uretdiones (cf. Proceedings of the International Waterborne, High-Solids, and Powder Coatings Symposium 2001, 28th, 405-419, and also US-A 2003 0153 713) to give allophanate structures, which have also been already successfully transposed to radiation-curing systems (German application No.: 102004012903, unpublished at the priority date of the present specification).

Both routes require high-grade raw materials as starting material and lead only to an allophanate product which is rich in by-products.

U.S. Pat. No. 5,777,024 describes the preparation of low-viscosity radiation-curing allophanates by reacting hydroxy-functional monomers which carry activated double bonds with isocyanate groups of allophanate-modified isocyanurate polyisocyanates. The radicals attached via the allophanate groups are saturated, and so any possible higher functionality is foregone.

EP-B 694 531 describes a multi-stage process for preparing hydrophilicized allophanates containing radiation-curing groups. In that case, however, first an NCO— and acrylate-functional urethane is prepared, which is then hydrophilicized and subsequently allophanatized following addition of a further NCO— and acrylate-functional urethane. As the process temperature for the allophanatization, temperatures of 100 to 110° C. are specified.

It was the object of the present invention, then, to provide, on the basis of readily available raw materials in one operation at a moderate temperature of below 100° C., and without a distillation step, an NCO-group-free, high-functionality allophanate mixture containing groups crosslinkable by actinic radiation (radiation-curing groups) as a radiation-curing binder, the intention being that this binder should have a residual diisocyanate monomer content of less than 0.5% by weight. The viscosity of this product ought to be sufficiently low, i.e. below 200 000 mPas @23° C., that it can be processed at room temperature even without addition of solvent.

SUMMARY OF THE INVENTION

It has now been found that radiation-curing allophanates of this kind, meeting the above-described requirements of the objective, can be prepared specifically when certain NCO/OH ratios are maintained during the preparation.

The invention provides a process for preparing radiation-curing allophanates having residual monomer contents of less than 0.5% by weight and an NCO content of less than 1% by weight, wherein
A) compounds containing isocyanate groups,
B) hydroxy-functional compounds which contain groups which react, with polymerization, with ethylenically unsaturated compounds on exposure to actinic radiation (radiation-curing groups) and
C) optionally further compounds containing NCO-reactive groups
D) optionally in the presence of a catalyst
are used to form NCO-group-containing urethanes having radiation-curing groups, which are subsequently reacted, without further addition of compounds containing isocyanate groups, in the presence
E) of an allophanatization catalyst,
the ratio of NCO groups of the compounds from A) to the OH groups of the compounds from B) and, where used, C) being 1.45:1.0 to 1.1:1.0.

Further provided by the invention are the binders obtainable by the process of the invention.

The invention further provides coating compositions comprising
a) one or more of the radiation-curing allophanates of the invention,
b) optionally one or more polyisocyanates containing free or blocked isocyanate groups, which are free from groups which react, with polymerization, with ethylenically unsaturated compounds on exposure to actinic radiation,
c) optionally other compounds, different from those of a), which contain groups which react, with polymerization, with ethylenically unsaturated compounds on exposure to actinic radiation, and optionally contain free or blocked NCO groups,
d) optionally one or more isocyanate-reactive compounds containing active hydrogen,
e) initiators,
f) optionally solvents and
g) optionally auxiliaries and additives.

DETAILED DESCRIPTION OF PREFERRED EMBODIMENTS

As used herein, as used in the examples or unless otherwise expressly specified, all numbers may be read as if prefaced by the word "about", even if the term does not expressly appear. Also, any numerical range recited herein is intended to include all sub-ranges subsumed therein.

The ratio of NCO groups of the compounds from A) to the OH groups of the compounds from B) and, where used, C) is preferably 1.43:1.0 to 1.2:1.0, more preferably 1.35:1.0 to 1.3:1.0.

Suitable isocyanate-containing compounds A) include aromatic, aliphatic and cycloaliphatic polyisocyanates. Suitable polyisocyanates are compounds of the formula $Q(NCO)_n$ having a number-average molecular weight below 800 g/mol, in which n is a number from 2 to 4 and Q is an aromatic $C_6$-$C_{15}$ hydrocarbon radical, an aliphatic $C_4$-$C_{12}$ hydrocarbon radical or a cycloaliphatic $C_6$-$C_{15}$ hydrocarbon radical. Suitability is possessed for example by diisocyanates from the series consisting of 2,4-/2,6-toluene diisocyanate (TDI), methylenediphenyl diisocyanate (MDI), triisocyanatononane (TIN), naphthyl diisocyanate (NDI), 4,4'-diisocyanatodicyclohexylmethane, 3-isocyanatomethyl-3,3,5-trimethylcyclohexyl isocyanate(isophorone diisocyanate=IPDI), tetramethylene diisocyanate, hexamethylene diisocyanate (HDI), 2-methylpentamethylene diisocyanate, 2,2,4-trimethylhexamethylene diisocyanate (THDI), dodecamethylene diisocyanate, 1,4-diisocyanatocyclohexane, 4,4'-diisocyanato-3,3'-dimethyldicyclohexylmethane, 2,2-bis(4-isocyanatocyclohexyl)propane, 3-isocyanatomethyl-1-methyl-1-isocyanatocyclohexane (MCI), 1,3-diisooctylcyanato-4-methylcyclohexane, 1,3-diisocyanato-2-methylcyclohexane and $\alpha,\alpha,\alpha',\alpha'$-tetramethyl-m- or -p-xylylene diisocyanate (TMXDI) and also mixtures consisting of these compounds.

Likewise suitable as isocyanate-containing compounds A) are reaction products of the aforementioned isocyanates with themselves or with one another to form uretdiones or isocyanurates. Mention may be made by way of example of Desmodur® N3300, Desmodur® N3400 or Desmodur® N3600 (all Bayer MaterialScience, Leverkusen, DE).

Of further suitability as isocyanate-containing compounds A) are reaction products of the aforementioned isocyanates with other isocyanate-reactive compounds to form prepolymers. Such isocyanate-reactive compounds are, in particular, polyols, such as polyether polyols, polyester polyols, polycarbonate polyols and polyhydric alcohols, for example. As polyols it is possible to use hydroxyl compounds of relatively high molecular weight and, in minor amounts, hydroxyl compounds of low molecular weight as well.

The compounds of component A) can accordingly be inserted directly into the process of the invention or, starting from an arbitrary precursor, can be prepared by preliminary reaction before the process of the invention is carried out.

Preference is given as component A) to the use of monomeric diisocyanates. Very particular preference is given to using hexamethylene diisocyanate (HDI), isophorone diisocyanate (IPDI) and/or 4,4'-diisocyanatodicyclohexylmethane.

By actinic radiation is meant electromagnetic, ionizing radiation, especially electron beams, UV radiation and also visible light (Roche Lexikon Medizin, 4th edition; Urban & Fischer Verlag, Munich 1999).

Groups which react, with polymerization, with ethylenically unsaturated compounds on exposure to actinic radiation (radiation-curing groups) are for the purposes of the present invention vinyl ether, maleyl, fumaryl, maleimide, dicyclopentadienyl, acrylamide, acrylic and methacrylic groups, preference being given to vinyl ether, acrylate and/or methacrylate groups, more preferably acrylate groups.

Examples of suitable hydroxyl-containing compounds of component B) are 2-hydroxyethyl(meth)acrylate, polyethylene oxide mono(meth)acrylate (e.g. PEA6/PEM6; Laporte Performance Chemicals Ltd., UK), polypropylene oxide mono(meth)acrylate (e.g. PPA6, PPM5S; Laporte Performance Chemicals Ltd., UK), polyalkylene oxide mono(meth)acrylate (e.g. PEM63P, Laporte Performance Chemicals Ltd., UK), poly(ε-caprolactone)mono(meth)acrylates such as, Tone M100® for example, (Dow, Schwalbach, DE), 2-hydroxypropyl(meth)acrylate, 4-hydroxybutyl(meth)acrylate, hydroxybutyl vinyl ether, 3-hydroxy-2,2-dimethylpropyl (meth)acrylate, the hydroxy-functional mono-, di- or where possible higher acrylates such as, for example, glyceryl di(meth)acrylate, trimethylolpropane di(meth)acrylate, pentaerythritol tri(meth)acrylate or dipentaerythritol penta(meth)acrylate, which are obtainable by reacting polyhydric, optionally alkoxylated alcohols such as trimethylolpropane, glycerol, pentaerythritol, dipentaerythritol.

Likewise suitable as a constituent of B) as well are alcohols obtained from the reaction of acids containing double bonds with epoxide compounds optionally containing double bonds, such as, for example, the reaction products of (meth) acrylic acid with glycidyl(meth)acrylate or bisphenol A diglycidyl ether.

Additionally it is likewise possible to use unsaturated alcohols which are obtained from the reaction of optionally unsaturated acid anhydrides with hydroxy compounds and epoxide compounds that optionally contain acrylate groups. By way of example these are the reaction products of maleic anhydride with 2-hydroxyethyl(meth)acrylate and glycidyl(meth) acrylate.

With particular preference the compounds of component B) correspond to the aforementioned kind and have an OH functionality of from 0.9 to 1.1.

Preference is given to the use of hydroxyethyl(meth)acrylate, hydroxypropyl(meth)acrylate and hydroxybutyl(meth) acrylate. Very particular preference is given to hydroxyethyl acrylate and hydroxypropyl acrylate.

Besides the OH-functional unsaturated compounds of component B) it is possible in the process of the invention to use further compounds C) as well, which are different from those of B) and contain NCO-reactive groups such as OH, SH or NH, for example.

These may be, for example, NH— or SH-functional compounds containing groups which react, with polymerization, with ethylenically unsaturated compounds on exposure to actinic radiation.

Compounds which are non-reactive under exposure to actinic rays, such as polyether polyols, polyester polyols, polycarbonate polyols and polyhydric alcohols, for example, can also be used in addition to influence the product properties, as component. C). As polyols it is possible to use hydroxyl compounds of relatively high molecular weight and, in minor amount, hydroxyl compounds of low molecular weight as well.

Hydroxyl compounds of relatively high molecular weight include the hydroxy polyesters, hydroxy polyethers, hydroxy polythioethers, hydroxy polyacetals, hydroxy polycarbonates, dimer fatty alcohols and/or esteramides that are customary in polyurethane chemistry, in each case with average molecular weights of 400 to 8000 g/mol, preference being given to those having average molecular weights of 500 to 6500 g/mol. Preferred hydroxyl compounds of relatively high molecular weight are hydroxy polyethers, hydroxy polyesters and hydroxy polycarbonates.

Low molecular weight polyhydroxyl compounds which can be used are polyols customary in polyurethane chemistry, having molecular weights of 62 to 399, such as ethylene glycol, triethylene glycol, tetraethylene glycol, propane-1,2-diol and -1,3-diol, butane-1,4-diol and -1,3-diol, hexane-1,6-diol, octane-1,8-diol, neopentyl glycol, 1,4-bis(hydroxymethyl)cyclohexane, bis(hydroxymethyl)tricyclo[5.2.1.0$^{2,6}$] decane or 1,4-bis(2-hydroxyethoxy)-benzene, 2-methyl-1,3-propanediol, 2,2,4-trimethylpentanediol, 2-ethyl-1,3-hexanediol, dipropylene glycol, polypropylene glycols, dibutylene glycol, polybutylene glycols, bisphenol A, tetrabromobisphenol A, glycerol, trimethylolpropane, hexane-1,2,6-triol-butane-1,2,4-triol, pentaerythritol, quinitol, mannitol, sorbitol, methyl glycoside and 4,3,6-dianhydrohexitols.

Suitable polyether polyols are the polyethers customary in polyurethane chemistry, such as the addition compounds or mixed addition compounds, prepared using starter molecules with a valency of two to six such as water or the abovementioned polyols or amines containing 1- to 4-NH bonds, of tetrahydrofuran, styrene oxide, ethylene oxide, propylene oxide, the butylene oxides or epichlorohydrin, particularly those of ethylene oxide and/or of propylene oxide. Preference is given to propylene oxide polyethers which contain on average 2 to 4 hydroxyl groups and which can contain up to 50% by weight of incorporated polyethylene oxide units.

Examples of suitable polyester polyols include reaction products of polyhydric, preferably dihydric and optionally additionally trihydric alcohols with polybasic, preferably dibasic, carboxylic acids. In lieu of the free carboxylic acids it is also possible to use the corresponding polycarboxylic anhydrides or corresponding polycarboxylic esters of lower alcohols or mixtures thereof for preparing the polyesters. The polycarboxylic acids may be aliphatic, cycloaliphatic aromatic and/or heterocyclic in nature and may where appropriate be substituted, by halogen atoms for example, and/or unsaturated. By way of example mention is made of adipic acid, phthalic acid, isophthalic acid, succinic acid, suberic acid, azelaic acid, sebacic acid, trimellitic acid, phthalic anhydride, tetrahydrophthalic anhydride, glutaric anhydride, tetrachlorophthalic anhydride, endomethylenetetrahydrophthalic anhydride, maleic anhydride, maleic acid, fumaric acid, dimeric and trimeric fatty acids such as oleic acid, optionally in a mixture with monomeric fatty acids, dimethyl terephthalate or bis-glycol terephthalate. Preference is given to hydroxy polyesters which melt at below 60° C. and have 2 or 3 terminal OH groups.

The polycarbonate polyols that come under consideration are obtainable by reacting carbonic acid derivatives, e.g. diphenyl carbonate, dimethyl carbonate or phosgene, with diols. Examples of suitable such diols include ethylene glycol, triethylene glycol, tetraethylene glycol, propane-1,2-diol and -1,3-diol, butane-1,4-diol and -1,3-diol, pentane-1,5-diol, hexane-1,6-diol, octane-1,8-diol, neopentyl glycol, 1,4-bis(hydroxymethyl)cyclohexane, bis(hydroxymethyl)tricyclo[5.2.1.0$^{2,6}$]decane or 1,4-bis(2-hydroxyethoxy)-benzene, 2-methyl-1,3-propanediol, 2,2,4-trimethylpentanediol, dipropylene glycol, polypropylene glycols, dibutylene glycol, polybutylene glycols, bisphenol A and tetrabromobisphenol A, or mixtures of said diols. The diol component preferably receives 40% to 100% by weight of hexanediol, preferably hexane-1,6-diol, and/or hexanediol derivatives, preferably those which in addition to terminal OH groups contain ether groups or ester groups, examples being products obtained by reacting 1 mol of hexanediol with at least 1 mol, preferably 1 to 2 mol, of caprolactone in accordance with DE-A 1 770 245, or by etherifying hexanediol with itself to give the di- or trihexylene glycol. The preparation of such derivatives is known for example from DE-A 1 570 540. The polyether-polycarbonate diols described in DE-A 3 717 060 can also be used to very good effect.

The hydroxypolycarbonates ought to be substantially linear. As a result of the incorporation of polyfunctional components, in particular polyols of low molecular weight, however, they may also, optionally, be slightly branched.

Examples of compounds suitable for this purpose include trimethylolpropane, hexane-1,2,6-triol, glycerol, butane-1,2,4-triol, pentaerythritol, quinitol, mannitol, sorbitol, methyl glycoside and 4,3,6-dianhydrohexitols.

Additionally it is possible to incorporate groups having a hydrophilicizing action, particularly if use from an aqueous medium is envisaged, such as in an aqueous coating material, for example. Groups with a hydrophilicizing action are ionic groups, which may be either cationic or anionic in nature, and/or nonionic hydrophilic groups. Cationically, anionically or nonionically dispersing compounds are those which contain, for example, sulphonium, ammonium, phosphonium, carboxylate, sulphonate or phosphonate groups or the groups which can be converted into the aforementioned groups by forming salts (potentially ionic groups) or which contain polyether groups and can be incorporated by means of existing isocyanate-reactive groups. Isocyanate-reactive groups of preferred suitability are hydroxyl and amino groups.

Examples of suitable compounds containing ionic or potentially ionic groups are mono- and dihydroxycarboxylic acids, mono- and diaminocarboxylic acids, mono- and dihydroxysuilphonic acids, mono- and diaminosulphonic acids and also mono- and dihydroxyphosphonic acids or mono- and diaminophosphonic acids and their salts, such as dimethylol propionic acid, dimethylolbutyric acid, hydroxypivalic acid, N-(2-aminoethyl)-β-alanine, 2-(2-aminoethylamino)ethanesulphonic acid, ethylenediamine-propyl- or butylsulphonic acid, 1,2- or 1,3-propylenediamine-β-ethylsulphonic acid, malic acid, citric acid, glycolic acid, lactic acid, glycine, alanine, taurine, lysine, 3,5-diaminobenzoic acid, an adduct of IPDI and acrylic acid (EP-A 0 916 647, Example 1) and its alkali metal and/or ammonium salts; the adduct of sodium bisulphite with but-2-ene-1,4-diol, polyethersulphonate, the propoxylated adduct of 2-butenediol and NaHSO$_3$, described for example in DE-A 2 446 440 (page 5-9, formula I-III) and also structural units which can be converted into cationic groups, such as N-methyldiethanolamine, as hydrophilic synthesis components. Preferred ionic or potential ionic compounds are those possessing carboxyl or carboxylate and/or sulphonate groups and/or ammonium groups.

Particularly preferred ionic compounds are those which contain carboxyl and/or sulphonate groups as ionic or potentially ionic groups, such as the salts of N-(2-aminoethyl)-β-alanine, of 2-(2-aminoethylamino)ethanesulphonic acid or of the adduct of IPDI and acrylic acid (EP-A-0 916 647, Example 1) and also of dimethylolpropionic acid.

Suitable nonionically hydrophilicizing compounds are, for example, polyoxyalkylene ethers containing at least one hydroxyl or amino group. These polyethers include a fraction of from 30% to 100% by weight of units derived from ethylene oxide. Suitable compounds include polyethers of linear construction with a functionality of between 1 and 3, but also compounds of the general formula (I),

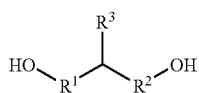

formula (I)

in which
$R^1$ and $R^2$ independently of one another are each a divalent aliphatic, cycloaliphatic or aromatic radical having 1 to 18 carbon atoms, which may be interrupted by oxygen and/or nitrogen atoms, and
$R^3$ is an alkoxy-terminated polyethylene oxide radical.

Nonionically hydrophilicizing compounds are, for example, also monohydric polyalkylene oxide polyether alcohols containing on average 5 to 70, preferably 7 to 55, ethylene oxide units per molecule, such as are obtainable in conventional manner by alkoxylating suitable starter molecules (e.g. in Ullmanns Encyclopädie der technischen Chemie, 4th edition, volume 19, Verlag Chemie, Weinheim pp. 31-38).

Examples of suitable starter molecules are saturated monoalcohols such as methanol, ethanol, n-propanol, isopropanol, n-butanol, isobutanol, sec-butanol, the isomers pentanols, hexanols, octanols and nonanols, n-decanol, n-dodecanol, n-tetradecanol, n-hexadecanol, n-octadecanol, cyclohexanol, the isomeric methylcyclohexanols or hydroxylmethylcyclohexane, 3-ethyl-3-hydroxymethyloxetane or tetrahydrofurfuryl alcohol, diethylene glycol monoalkyl ethers such as, for example, diethylene glycol monobutyl ether, unsaturated alcohols such as allyl alcohol, 1,1-dimethylallyl alcohol or oleyl alcohol, aromatic alcohols such as phenol, the isomeric cresols or methoxyphenols, araliphatic alcohols such as benzyl alcohol, anisyl alcohol or cinnamyl alcohol, secondary monoamines such as dimethylamine, diethylamine, dipropylamine, diisopropylamine, dibutylamine, bis(2-ethylhexyl)amine, N-methyl- and N-ethylcyclohexylamine or dicyclohexylamine and also heterocyclic secondary amines such as morpholine, pyrrolidine, piperidine or 1H-pyrazole. Preferred starter molecules are saturated monoalcohols. Particular preference is given to using diethylene glycol monobutyl ether as starter molecule.

Alkylene oxides suitable for the alkoxylation reaction are, in particular, ethylene oxide and propylene oxide, which can be used in any order or in a mixture in the alkoxylation reaction.

The polyalkylene oxide polyether alcohols are either straight polyethylene oxide polyethers or mixed polyalkylene oxide polyethers at least 30 mol %, preferably at least 40 mol %, of whose alkylene oxide units are composed of ethylene oxide units. Preferred nonionic compounds are monofunctional mixed polyalkylene oxide polyethers which contain at least 40 mol % of ethylene oxide units and not more than 60 mol % of propylene oxide units.

Especially when using a hydrophilicizing agent containing ionic groups it is necessary to investigate its effect on the action of the catalysts D) and E). For this reason preference is given to nonionic compounds as hydrophilicizing agents.

Suitable compounds of the catalyst component D) include urethanization catalysts that are known per se to the skilled person, such as organotin compounds or aminic catalysts. Organotin compounds that may be mentioned by way of example include the following: dibutyltin diacetate, dibutyltin dilaurate, dibutyltin bis-acetoacetonate and tin carboxylates such as tin octoate, for example. The tin catalysts mentioned may optionally be used in combination with aminic catalysts such as aminosilanes or 1,4-diazabicyclo[2.2.2]octane.

With particular preference dibutyltin dilaurate is used as urethanization catalyst in D).

In the process of the invention the catalyst D), if used at all, is employed in amounts of 0.001% to 5.0%, preferably 0.001% to 0.1% and more preferably 0.005%-to 0.05% by weight, based on solids content of the process product.

As catalyst E) it is possible to use allophanatization catalysts that are known per se to the skilled person, such as the zinc salts zinc octoate, zinc acetylacetonate and zinc 2-ethylcaproate, or tetraalkylammonium compounds, such as N,N,N-trimethyl-N-2-hydroxypropylammonium hydroxide, N,N,N-trimethyl-N-2-hydroxypropylammonium 2-ethylhexanoate or choline 2-ethylhexanoate. Preference is given to the use of the tetraalkylammonium compounds, more preferably that of tetraalkylammonium alkanoates and very preferably that of choline 2-ethylhexanoate as allophanatization catalyst.

The allophanatization catalyst is used in amounts of 0.001-5.0% by weight, preferably 0.01-1.0% by weight and more preferably 0.05-0.5% by weight based on solids content of the process product.

In principle it is possible to use the allophanatization catalyst E) even for the urethanization reaction in D) and to simplify the two-stage procedure into a one-stage reaction. However, this is not preferred, and so the allophanatization catalyst is not added until all or a proportion of the urethane groups are to be reacted to allophanate groups.

The catalyst E) can be added in a portion all at once or else in a number of portions or else continuously. Preference is given to portionwise or continuous addition, in order to avoid temperature peaks and consequent unwanted polymerization reactions of the radiation-curing groups. With particular preference the catalyst E) is added at a rate of 200-600 ppm/h and in order to complete the allophanatization the reaction mixture is stirred on until the desired NCO content of the end product is reached.

The reaction of allophanatization is preferably carried out until the NCO content of the product is below 0.5% by weight, more preferably below 0.1% by weight.

It is possible in principle to react a residual NCO group content with NCO-reactive compounds such as alcohols, for example, after the end of the allophanatization reaction. This gives products having a specially low NCO contents.

It is also possible to apply the catalysts D) and/or E) to support materials by methods known to the skilled person and to use them as heterogeneous catalysts.

It is possible to make use optionally at any desired point of solvents or reactive diluents.

Suitable solvents are inert towards the functional groups present in the process product from the time of their addition up to the end of the process. Suitable solvents are, for example, those used in the paint industry, such as hydrocarbons, ketones and esters, e.g. toluene, xylene, isooctane, acetone, butanone, methyl isobutyl ketone, ethyl acetate, butyl acetate, tetrahydrofuran, N-methylpyrrolidone, dimethylacetamide and dimethylformamide, though it is preferred not to add any solvent.

As reactive diluents it is possible to use compounds which in the course of UV curing are likewise (co)polymerized and hence incorporated into the polymer network and are inert towards NCO groups. Such reactive diluents are described exemplarily, by way of example, in P. K. T. Oldring (Ed.), Chemistry & Technology of UV & EB Formulations For Coatings, Inks & Paints, Vol. 2, 1991, SITA Technology, London, pp. 237-285. They may be esters of acrylic acid or methacrylic acid, preferably of acrylic acid, with mono- or polyfunctional alcohols. Examples of suitable alcohols include the isomeric butanols, pentanols, hexanols, heptanols, octanols, nonanols and decanols, and also cycloaliphatic alcohols such as isobornol, cyclohexanol and alkylated cyclohexanols, dicyclo-pentanol, arylaliphatic alcohols such as phenoxyethanol and nonylphenylethanol, and tetrahydrofurfuryl alcohols. Additionally it is possible to use alkoxylated derivatives of these alcohols. Suitable dihydric alcohols are, for example, alcohols such as ethylene glycol, propane-1,2-diol, propane-1,3-diol, diethylene glycol, dipropylene glycol, the isomeric butanediols, neopentyl glycol, hexane-1,6-diol, 2-ethylhexanediol and tripropylene glycol or else alkoxylated derivatives of these alcohols. Preferred dihydric alcohols are hexane-1,6-diol, dipropylene glycol and tripropylene glycol. Suitable trihydric alcohols are glycerol or trimethylolpropane or their alkoxylated derivatives. Tetrahydric alcohols are pentaerythritol or its alkoxylated derivatives.

The binders of the invention must be stabilized against premature polymerization. Therefore, as a constituent of component A) or B), before and/or during the reaction, stabilizers are added which inhibit the polymerization. Use is made in this context preferably of phenothiazine. Possible other stabilizers are phenols such as para-methoxyphenyl, 2,5-di-tert-butylhydroquinone or 2,6-di-tert-butyl-4-methylphenol. Also suitable are N-oxyl compounds for stabilization, such as 2,2,6,6-tetramethylpiperidine N-oxide (TEMPO), for example, or its derivatives. The stabilizers can also be incorporated chemically into the binder; suitability in this context is possessed by compounds of the abovementioned classes, especially if they still carry further free aliphatic alcohol groups or primary or secondary amine groups and hence can be attached chemically to compounds of component A) by way of urethane or urea groups. Particularly suitable for this purpose is 2,2,6,6-tetramethyl-4-hydroxypiperidine N-oxide.

Other stabilizers, such as compounds from the class of the HALS (HALS=hindered amine light stabilizers), in contrast, are used less preferably in E), since they are known not to enable such effective stabilization and instead may lead to "creeping" free-radical polymerization of unsaturated groups.

The stabilizers are to be chosen such that they are stable under the influence of the catalysts D) and E) and do not react with a component of the process of the invention under the reaction conditions. This can lead to a loss of the stabilizing property.

In order to stabilize the reaction mixture, in particular the unsaturated groups, against premature polymerization it is possible to pass an oxygen-containing gas, preferably air, into and/or over the reaction mixture. It is preferred for the gas to have a very low moisture content, in order to prevent unwanted reaction in the presence of isocyanate.

In general a stabilizer is added during the preparation of the binders of the invention, and at the end, in order to achieve a long-term stability, stabilization is repeated with a phenolic stabilizer, and optionally the reaction product is saturated with air.

In the process of the invention the stabilizer component is used typically in amounts of 0.001% to 5.0% by weight, preferably 0.01% to 2.0% by weight and more preferably 0.05% to 1.0% by weight, based on the solids content of the process product.

The process of the invention is carried out at temperatures of not more than 100° C., preferably of 20 to 100° C., more preferably of 40 to 100° C., in particular at 60 to 90° C.

It is immaterial whether one or both stages of the process of the invention is or are carried out continuously in for example a static mixer, extruder or compounder or batchwise in for example a stirred reactor.

Preferably the process of the invention is carried out in a stirred reactor.

The course of the reaction can be monitored by means of suitable measuring instruments installed in the reaction vessel and/or on the basis of analyses on samples taken. Suitable techniques are known to the skilled person. They include, for example, viscosity measurements, measurements of the NCO content, of the refractive index, of the OH content, gas chromatography (GC), nuclear magnetic resonance spectroscopy (NMR), infrared spectroscopy (IR) and near infrared spectroscopy (NIR). Preference is given to IR checking for free NCO groups present (for aliphatic NCO groups, band at approximately $v=2272$ cm$^{-1}$) and to GC analyses for unreacted compounds from A), B) and, where used, C).

It is possible in principle to carry out the process of the invention in one stage, operating with a catalyst or a catalyst mixture that catalyses both the urethanization reaction and the allophanatization reaction. In that case urethanization and allophanatization are carried out in parallel. This procedure, though, is not preferred.

The unsaturated allophanates obtainable by the process of the invention, especially those based on the HDI employed with preference, preferably have shear viscosities at 23° C. of ≤150 000 mPas, more preferably ≤80 000 mPas.

The unsaturated allophanates obtainable by the process of the invention, especially those based on the HDI used with preference, preferably have number-average molecular weights $M_n$ of 600 to 3000 g/mol, more preferably 650 to 1500 g/mol.

The unsaturated allophanates obtainable by the process of the invention preferably contain less than 0.5% by weight of free di- and/or triisocyanate monomers, more preferably less than 0.1% by weight.

The radiation-curing allophanates of the invention can be used for producing coatings and paints and also adhesives, printing inks, casting resins, dental compounds, sizes, photoresists, stereolithography systems, resins for composite materials and sealants. In the case of adhesive bonding or sealing, however, a requirement is that, in the case of UV radiation curing, at least one of the two substrates to be bonded or sealed to one another is permeable to UV radiation; in other words, in general, it must be transparent. In the case of electron beams, sufficient permeability for electrons should be ensured. Preference is given to use in paints and coatings.

The invention further provides coating compositions comprising a) one or more of the radiation-curing allophanates of the invention,
b) optionally one or more polyisocyanates containing free or blocked isocyanate groups, which are free from groups which react, with polymerization, with ethylenically unsaturated compounds on exposure to actinic radiation,
c) optionally other compounds, different from those of a), which contain groups which react, with polymerization, with ethylenically unsaturated compounds on exposure to actinic radiation, and optionally contain free or blocked NCO groups,
d) optionally one or more isocyanate-reactive compounds containing active hydrogen,
e) initiators,
f) optionally solvents and
g) optionally auxiliaries and additives.

The polyisocyanates of component b) are known per se to the skilled person. Preference is given here to using compounds optionally modified with isocyanurate, allophanate, biuret, uretdione and/or iminooxadiazinetrione groups and based on hexamethylene diisocyanate, isophorone diisocyanate, 4,4'-diisocyanatodicyclohexylmethane and/or trimethylhexamethylene diisocyanate.

The NCO groups in this case may also be blocked, blocking agents employed being the compounds already mentioned in connection with the description of component A).

The compounds of component c) include compounds such as, in particular, urethane acrylates based preferably on hexamethylene diisocyanate, isophorone diisocyanate, 4,4'-diisocyanatodicyclohexylmethane and/or trimethylhexamethylene diisocyariate, which optionally may have been modified with isocyanurate, allophanate, biuret, uretdione and/or iminooxadiazinetrione groups, and which contain no isocyanate-group-reactive functions containing active hydrogen.

NCO-containing urethane acrylates are available commercially from Bayer AG, Leverkusen, DE as Roskydal® UA VP LS 2337, Roskydal® UA VP LS 2396 or Roskydal® UA XP 2510.

Additionally the reactive diluents already described and known in the art of radiation-curing coatings may be used as a constituent of c), provided that they do not contain any NCO-reactive groups.

Compounds of component d) can be saturated or unsaturated. Chemical functionalities reacting with NCO groups are functionalities containing activated hydrogen atoms, such as hydroxyl, amine or thiol.

Preference is given to saturated polyhydroxy compounds, examples being the polyetherpolyols, polyesterpolyols, polycarbonatepolyols, poly(meth)acrylatepolyols and/or polyurethanepolyols which are known from the technology of coating, adhesive bonding, printing inks or sealants and which contain no groups which react, with polymerization, with ethylenically unsaturated compounds on exposure to actinic radiation.

Unsaturated hydroxy-functional compounds are, for example, the epoxy acrylates, polyester acrylates, polyether acrylates, urethane acrylates and acrylated polyacrylates which are known in the art of radiation-curing coatings and have an OH number of from 30 to 300 mg KOH/g.

It is additionally possible to use the reactive diluents, already described and known in the art of radiation-curing coatings, as a constituent of d), provided that they contain NCO-reactive groups.

As initiators of component e) for a free-radical polymerization it is possible to employ initiators which can be activated thermally and/or by radiation. Photoinitiators, which are activated by UV or visible light, are preferred in this context. Photoinitiators are compounds known per se, being sold commercially, a distinction being made between unimolecular (type I) and bimolecular (type II) initiators. Suitable (type I) systems are aromatic ketone compounds, e.g. benzophenones in combination with tertiary amines, alkylbenzophenones, 4,4'-bis(dimethylamino)benzophenone (Michler's ketone), anthrone and halogenated benzophenones or mixtures of the types stated. Of further suitability are (type II) initiators such as benzoin and its derivatives, benzil ketals, acylphosphine oxides, 2,4,6-trimethylbenzoyldiphenylphosphine oxide for example, bisacylphosphine oxides, phenylglyoxylic esters, camphorquinone, α-aminoalkylphenones, α,α-dialkoxyacetophenones and α-hydroxyalkylphenones.

The initiators, which are used in amounts between 0.1% and 10% by weight, preferably 0.1% to 5% by weight, based on the weight of the film-forming binder, can be used as an individual substance or, on account of frequent advantageous synergistic effects, in combination with one another.

Where electron beams are used instead of UV radiation there is no need for a photoinitiator. Electron beams, as is known to the skilled person, are generated by means of thermal emission and accelerated by way of a potential difference. The high-energy electrons then pass through a titanium foil and are guided onto the binders to be cured. The general principles of electron beam curing are described in detail in "Chemistry & Technology of UV & EB Formulations for Coatings, Inks & Paints", Vol. 1, P K T Oldring (Ed.), SITA Technology, London, England, pp. 101-157, 1991.

In the event of thermal curing of the activated double bonds, this can also take place with addition of thermally decomposing free-radical initiators. Suitability is possessed, as is known to the skilled person, by, for example, peroxy compounds such as dialkoxy dicarbonates such as, for example, bis(4-tert-butylcyclohexyl)peroxydicarbonate, dialkyl peroxides such as, for example, dilauryl peroxide, peresters of aromatic or aliphatic acids such as, for example, tert-butyl perbenzoate or tert-amyl peroxy 2-ethylhexanoate, inorganic peroxides such as, for example, ammonium peroxodisulphate, potassium peroxodisulphate, organic peroxides such as, for example, 2,2-bis(tert-butylperoxy)butane, dicumyl peroxide, tert-butyl hydroperoxide or else azo compounds such as 2,2'-azobis[N-(2-propenyl)-2-methylpropionamides], 1-[(cyano-1-methylethyl)azo]formamides, 2,2'-azobis(N-butyl-2-methylpropionamides), 2,2'-azobis(N-cyclohexyl-2-methyl-propionamides), 2,2'-azobis{2-methyl-N-[2-(1-hydroxybutyl)]propionamides}, 2,2'-azobis{2-methyl-N-[2-(1-hydroxybutyl)]propionamides, 2,2'-azobis{2-methyl-N-[1,1-bis(hydroxymethyl)-2-hydroxyethyl]propionamides. Also possible are highly substituted 1,2-diphenylethanes(benzpinacols), such as, for example, 3,4-dimethyl-3,4-diphenylhexane, 1,1,2,2-tetraphenylethane-1,2-diol or else the silylated derivatives thereof.

It is also possible to use a combination of initiators activable by UV light and thermally.

The auxiliaries and additives of component e) include solvents of the type specified above.

Additionally it is possible for e), in order to increase the weather stability of the cured coating film, to comprise UV absorbers and/or HALS stabilizers as well. Preference is given to the combination. The former ought to have an absorption range of not more than 390 nm, such as triphenyltriazine types (e.g. Tinuvin® 400 (Ciba Spezialitätenchemie GmbH, Lampertheim, DE)), benzotriazoles such as Tinuvin® 622 (Ciba Spezialitätenchemie GmbH, Lampertheim, DE) or oxalic dianilides (e.g. Sanduvor® 3206 (Clariant, Muttenz, CH))) and are added at 0.5%-3.5% by weight, based on resin solids. Suitable HALS stabilizers are available commercially (Tinuvin® 292 or Tinuvin® 123 (Ciba Spezialitätenchemie GmbH, Lampertheim, DE) or Sanduvor® 3258 (Clariant, Muttenz, CH). Preferred amounts are 0.5%-2.5% by weight based on resin solids.

It is likewise possible for e) to comprise pigments, dyes, fillers, levelling additives and devolatilizing additives.

Additionally it is possible, if necessary, for the catalysts known from polyurethane chemistry for accelerating the NCO/OH reaction to be present in e). These are, for example, tin salts or zinc salts or organotin compounds, tin soaps and/or zinc soaps such as, for example, tin octoate, dibutyltin dilaurate, dibutyltin oxide or tertiary amines such as diazabicyclo [2.2.2]octane (DABCO).

The application of the coating compositions of the invention to the material to be coated takes place with the methods known and customary in coatings technology, such as spraying, knife coating, rolling, pouring, dipping, spin coating, brushing or squirting or by means of printing techniques such as screen, gravure, flexographic or offset printing and also by means of transfer methods.

Suitable substrates are, for example, wood, metal, including in particular metal as used in the applications of wire enamelling, coil coating, can coating or container coating, and also plastic, including plastic in the form of films, especially ABS, AMMA, ASA, CA, CAB, EP, UF, CF, MF, MPF, PF, PAN, PA, PE, HDPE, LDPE, LLDPE, UHMWPE, PET, PMMA, PP, PS, SB, PUR, PVC, RF, SAN, PBT, PPE, POM, PUR-RIM, SMC, BMC, PP-EPDM, and UP (abbreviations according to DIN 7728T1), paper, leather, textiles, felt, glass, wood, wood materials, cork, inorganically bonded substrates such as wooden boards and fibre cement slabs, electronic assemblies or mineral substrates. It is also possible to coat substrates consisting of a variety of the abovementioned materials, or to coat already coated substrates such as vehicles, aircraft or boats and also parts thereof, especially vehicle bodies or parts for exterior mounting. It is also possible to apply the coating compositions to a substrate temporarily, then to cure them partly or fully and optionally to detach them again, in order to produce films, for example.

For curing it is possible for solvents present, for example, to be removed entirely or partly by flashing off.

Subsequently or simultaneously it is possible for the optionally necessary thermal and photochemical curing operation or operations to be carried out in succession or simultaneously.

If necessary the thermal curing can take place at room temperature or else at elevated temperature, preferably at 40 to 160° C., more preferably at 60 to 130° C., very preferably at 80 to 110° C.

Where photoinitiators are used in d) the radiation cure takes place preferably by exposure to high-energy radiation, in other words UV radiation or daylight, such as light of wavelength 200 to 700 nm or by bombardment with high-energy electrons (electron beams, 150 to 300 keV). Radiation sources of light or UV light used are, for example, high-pressure or medium-pressure mercury vapour lamps, it being possible for the mercury vapour to have been modified by doping with other elements such as gallium or iron. Lasers, pulsed lamps (known under the designation of UV flashlight lamps), halogen lamps or excimer emitters are likewise possible. As an inherent part of their design or through the use of special filters and/or reflectors, the emitters may be equipped so that part of the UV spectrum is prevented from being emitted. By way of example, for reasons of occupational hygiene, for example, the radiation assigned to UV-C or to UV-C and UV-B may be filtered out. The emitters may be installed in stationary fashion, so that the material for irradiation is conveyed past the radiation source by means of a mechanical device, or the emitters may be mobile and the material for irradiation may remain stationary in the course of curing. The radiation dose which is normally sufficient for crosslinking in the case of UV curing is situated in the range from 80 to 5000 mJ/cm$^2$.

Irradiation can if desired also be carried out in the absence of oxygen, such as under an inert gas atmosphere or an oxygen-reduced atmosphere. Suitable inert gases are preferably nitrogen, carbon dioxide, noble gases or combustion gases. Irradiation may additionally take place by covering the coating with media transparent to the radiation. Examples of such are, for example, polymeric films, glass or liquids such as water.

Depending on the radiation dose and curing conditions it is possible to vary the type and concentration of any initiator used, in a manner known to the skilled person.

Particular preference is given to carrying out curing using high-pressure mercury lamps in stationary installations. Photoinitiators are then employed at concentrations of from 0.1% to 10% by weight, more preferably from 0.2% to 3.0% by weight, based on the solids of the coating. For curing these coatings it is preferred to use a dose of from 200 to 3000 mJ/cm$^2$, measured in the wavelength range from 200 to 600 nm.

In the case of use of thermally activable initiators in d) the curing can be carried out by increasing the temperature. The thermal energy may in this case be introduced into the coating by means of radiation, thermal conduction and/or convection, it being customary to employ the infrared lamps, near-infrared lamps and/or ovens that are conventional in coatings technology.

The applied film thicknesses (prior to curing) are typically between 0.5 and 5000 μm, preferably between 5 and 1000 μm, more preferably between 15 and 200 μm. Where solvents are used, it is removed after application and before curing, by the customary methods.

EXAMPLES

All percentages are by weight unless indicated otherwise.

The determination of the NCO contents in % was undertaken by back-titration with 0.1 mol/l hydrochloric acid following reaction with butylamine, on the basis of DIN EN ISO 11909.

The Viscosity Measurements were Carried Out with a Plate-Plate Viscometer Roto Visko 1 from Haake, DE In Accordance with ISO/DIS 3219:1990.

The ambient temperature of 23° C. prevailing at the time when the experiments were conducted is referred to as RT.

Preparation of Choline 2-Ethylhexanoate

In a 1000 ml glass flask with stirring apparatus 83 g of sodium 2-ethylhexanoate were dissolved at RT in 600 ml of methanol. Subsequently 69.8 g of choline chloride were added in portions and the mixture was stirred at room temperature for a further 10 hours. The precipitate formed was filtered off and the solution was concentrated to roughly a third under reduced pressure on a rotary evaporator until again a precipitate formed. Dilution took place with about 400 ml of acetone, followed by filtration again, and the solvent was again stripped off under reduced pressure. The residue which remained was again taken up in about 400 ml of acetone, followed by filtration, and the solvent was stripped off. This gave 117 g of crystallization-stable, liquid product which was used in this form as an allophanatization catalyst.

Example 1

Inventive Allophanate-Containing Binder (NCO/OH=1.33:1)

A 500-ml four-necked glass flask with reflux condenser, heatable oil bath, mechanical stirrer, air traversal (l/h), internal thermometer and dropping funnel was charged with 231.16 g of hexamethylene diisocyanate (Desmodur® H, Bayer MaterialScience, Leverkusen) and 50 mg of phenothiazine and this initial charge was heated to 70° C. 25 mg of dibutyltin dilaurate (Desmorapid Z, Bayer MaterialScience, Leverkusen) were added and 268.01 g of hydroxypropyl acrylate were added dropwise at a rate such that the temperature did not exceed 80° C.

Stirring was then continued until the theoretical NCO value of 5.77% was reached. Subsequently the temperature was raised to 80° C. and over 6 hours 0.75 g of choline 2-ethylhexanoate was slowly metered in. After about more than half the time a distinct exotherm was observed, which necessitated cooling of the mixture. Despite this, metering was completed, and was followed by stirring for an additional two hours. This gave a colourless resin having a residual NCO content of 0.1% and a viscosity of 75,400 mPas (23° C.).

Example 2

Inventive Allophanate-Containing Binder (NCO/OH=1.25:1)

A 500-ml four-necked glass flask with reflux condenser, heatable oil bath, mechanical stirrer, air traversal (l/h), internal thermometer and dropping funnel was charged with 223.18 g of hexamethylene diisocyanate and 50 mg of phenothiazine and this initial charge was heated to 70° C. 25 mg of dibutyltin dilaurate were added and 276.00 g of hydroxypropyl acrylate were added dropwise at a rate such that the temperature did not exceed 80° C. Stirring was then continued until the theoretical NCO value of 4.46% was reached. Subsequently at 70° C. over 6 hours 0.75 g of choline 2-ethylhexanoate was slowly metered in. Towards the end of the time a distinct exotherm was observed, which necessitated cooling of the mixture. Despite this, metering was completed, and was followed by stirring for an additional two hours. This gave a colourless resin having a residual NCO content of 0.05% and a viscosity of 35,800 mPas (23° C.).

Example 3

Inventive Allophanate-Containing Binder (NCO/OH=1.43:1)

A 500-ml four-necked glass flask with reflux condenser, heatable oil bath, mechanical stirrer, air traversal (l/h), internal thermometer and dropping funnel was charged with 239.74 g of hexamethylene diisocyanate and 50 mg of phenothiazine and this initial charge was heated to 70° C. 25 mg of dibutyltin dilaurate were added and 259.43 g of hydroxypropyl acrylate were added dropwise at a rate such that the temperature did not exceed 80° C. Stirring was then continued until the theoretical NCO value of 7.18% was reached. Subsequently at 70° C. over 6 hours 0.75 g of choline 2-ethylhexanoate was slowly metered in. After about more than half the time a distinct exotherm was observed, which necessitated cooling of the mixture. Despite this, metering was completed, and was followed by stirring for an additional hour. This gave a colourless resin having a residual NCO content of 0.0% and a viscosity of 125,000 mPas (23° C.).

Comparative Example to Example 1-3

Non-Inventive Allophanate-Containing Binder (NCO/OH=1.6:1)

A 500-ml four-necked glass flask with reflux condenser, heatable-oil bath, mechanical stirrer, air traversal (l/h), internal thermometer and dropping funnel was charged with 268.8 g of hexamethylene diisocyanate and 50 mg of phenothiazine and this initial charge was heated to 70° C. 25 mg of dibutyltin dilaurate were added and 260.0 g of hydroxypropyl acrylate were added dropwise at a rate such that the temperature did not exceed 80° C. Stirring was then continued until the theoretical NCO value of 9.53% was reached. Subsequently at 70° C. over 6 hours 0.75 g of choline 2-ethylhexanoate was slowly metered in. Towards the end of the time a distinct exotherm was observed, which necessitated cooling of the mixture. Despite this, metering was completed, and was followed by stirring for an additional two hours. This gave a colourless resin having a residual NCO content of 0.05% and a viscosity, extremely difficult to measure, of about 650,000 mPas (23° C.).

Example 4

Inventive Allophanate-Containing Binder (Hybrid Type, NCO/OH=1.33:1)

A 500-ml four-necked glass flask with reflux condenser, heatable oil bath, mechanical stirrer, air traversal (l/h), internal thermometer and dropping funnel was charged with a mixture of 107.59 g of hexamethylene diisocyanate and 142.02 of isophorone diisocyanate (Desmodur® I, Bayer MaterialScience, Leverkusen) with 250 mg of phenothiazine and this initial charge was heated to 70° C. 50 mg of dibutyltin dilaurate were added and 249.49 g of hydroxypropyl acrylate were added dropwise at a rate such that the temperature did not exceed 80° C. Stirring was continued until the theoretical NCO value of 5.37% was reached. Subsequently the temperature was raised to 80° C. and over 4 hours 0.75 g of choline 2-ethylhexanoate was slowly metered in. After about half the time a distinct exotherm was observed, which necessitated cooling of the mixture. After the end of the metering, stirring was continued for an additional two hours and dilution took place with 125 g of hexanediol diacrylate (Laromer® HDDA, BASF AG, Ludwigshafen, DE). This gave a yellowish resin having a residual NCO content of 0.17% and a viscosity of 20,500 mPas (23° C.).

Example 5

Coating Formulation and Coating Material

A portion of the product from Example 1 was mixed thoroughly with 3.0% of the photoinitiator Darocur® 1173 (photoinitiator, commercial product of Ciba Spezialitätenchemie GmbH, Lampertheim, DE). Using a bone doctor blade with a gap of 90 μm the mixture was drawn down in the form of a thin film onto a glass plate. UV irradiation (medium pressure mercury lamp, IST Metz GmbH, Nürtingen, DE, 750 mJ/cm$^2$) gave a hard, transparent coating which could hardly be damaged by scratching using steel wool (grade 0/0/0) in ten back-and-forth strokes with a force of 500 g directed onto the film.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing radiation-curing allophanates having residual monomer content of less than 0.5% by weight and an NCO content of less than 1% by weight, wherein
    A) compounds containing isocyanate groups,
    B) hydroxy-functional compounds which contain at least one group selected from vinyl ethers, acrylates and methacrylates which react, with polymerization, with ethylenically unsaturated compounds on exposure to actinic radiation and
    C) optionally further compounds containing NCO-reactive groups
    D) optionally in the presence of a catalyst
    are used to form NCO-group-containing urethanes having radiation-curing groups, which are subsequently reacted, without further addition of compounds containing isocyanate groups, in the presence
    E) of an allophanatization catalyst,
        the ratio of NCO groups of the compounds from A) to the OH groups of the compounds from B) and, where used, C) being 1.45:1.0 to 1.1:1.0, and
    wherein no distillation is required to yield the radiation-curing allophanates having a residual monomer content of less than 0.5% by weight and an NCO content of less than 1% by weight.

2. Process for preparing radiation-curing allophanates according to claim 1, wherein in component A) hexamethylene diisocyanate (HDI), isophorone diisocyanate (IPDI) and/or 4,4'-diisocyanatodicyclohexylmethane are used.

3. Process for preparing radiation-curing allophanates according to claim 1, wherein in component B) hydroxyethyl (meth)acrylate, hydroxypropyl (meth)acrylate and/or hydroxybutyl (meth)acrylate are used.

4. Process for preparing radiation-curing allophanates according to claim 1, wherein the ratio of NCO groups of the compounds from A) to the OH groups of the compounds from B) and, where used, C) is 1.35:1.0 to 1.3:1.0.

5. Process for preparing radiation-curing allophanates according to claim 1, wherein catalyst E) is added at a rate of 200-600 ppm/h.

6. Process for preparing radiation-curing allophanates according to claim 1, wherein the allophanatization is carried out until the end product has an NCO content of below 0.1% by weight.

7. Process for preparing radiation-curing allophanates comprising reacting, optionally in the presence of a catalyst,
    A) compounds containing isocyanate groups,
    B) hydroxy-functional compounds which contain at least one group selected from vinyl ethers, acrylates and methacrylates which react, with polymerization, with ethylenically unsaturated compounds on exposure to actinic radiation and
    C) optionally further compounds containing NCO-reactive groups to form NCO-group-containing urethanes having radiation-curing groups, and subsequently reacting the NCO-group containing urethanes, without further addition of compounds containing isocyanate groups, in the presence
    E) of an allophanatization catalyst,
    to form the radiation-curing allophanates,
    wherein the ratio of NCO groups of the compounds from A) to the OH groups of the compounds from B) and, where used, C) is from 1.45:1.0 to 1.1:1.0,
    wherein the radiation-curing allophanates have an NCO content of less than 1% by weight and have a residual monomer content of less than 0.5% by weight,
    with the proviso that no distillation step is performed.

8. Process for preparing radiation-curing allophanates according to claim 7, wherein in component A) hexamethylene diisocyanate (HDI), isophorone diisocyanate (IPDI) and/or 4,4'-diisocyanatodicyclohexylmethane are used.

9. Process for preparing radiation-curing allophanates according to claim 7, wherein in component B) hydroxyethyl (meth)acrylate, hydroxypropyl (meth)acrylate and/or hydroxybutyl (meth)acrylate are used.

10. Process for preparing radiation-curing allophanates according to claim 7, wherein the ratio of NCO groups of the compounds from A) to the OH groups of the compounds from B) and, where used, C) is 1.35:1.0 to 1.3:1.0.

11. Process for preparing radiation-curing allophanates according to claim 7, wherein catalyst E) is added at a rate of 200-600 ppm/h.

12. Process for preparing radiation-curing allophanates according to claim 7, wherein the allophanatization is carried out until the end product has an NCO content of below 0.1% by weight.

* * * * *